(12) United States Patent
Myllykangas et al.

(10) Patent No.: US 12,144,628 B2
(45) Date of Patent: Nov. 19, 2024

(54) DISPOSABLE PATCH ELECTRODE STRUCTURE AND CONNECTOR OF BIO-SIGNAL MEASUREMENT SYSTEM, BIO-SIGNAL MEASUREMENT SYSTEM AND METHOD OF CONNECTING WITH DISPOSABLE PATCH ELECTRODE STRUCTURE

(71) Applicant: Bittium Biosignals Oy, Kuopio (FI)

(72) Inventors: Juha Myllykangas, Kuopio (FI); Arto Nikula, Kuopio (FI)

(73) Assignee: BITTIUM BIOSIGNALS OY, Kuopio (FI)

(*) Notice: Subject to any disclaimer, the term of this patent is extended or adjusted under 35 U.S.C. 154(b) by 774 days.

(21) Appl. No.: 17/342,724

(22) Filed: Jun. 9, 2021

(65) Prior Publication Data

US 2022/0395211 A1 Dec. 15, 2022

(51) Int. Cl.
*A61B 5/273* (2021.01)
*A61B 5/28* (2021.01)
*A61B 5/291* (2021.01)

(52) U.S. Cl.
CPC ............. *A61B 5/28* (2021.01); *A61B 5/273* (2021.01); *A61B 5/291* (2021.01); *A61B 2562/225* (2013.01)

(58) Field of Classification Search
CPC ...... A61B 2562/225–228; A61B 5/273; A61B 5/274; A61B 2560/0412;

(Continued)

(56) References Cited

U.S. PATENT DOCUMENTS

| 2004/0009731 A1* | 1/2004 | Rabinowicz ............. A61N 1/04 2/456 |
| 2011/0279963 A1 | 11/2011 | Kumar et al. |
| 2021/0128042 A1 | 5/2021 | Herberger |

FOREIGN PATENT DOCUMENTS

WO 2017/039518 3/2017
WO WO-2017039518 A1 * 3/2017

OTHER PUBLICATIONS

Extended European Search Report issued on Nov. 23, 2022 in corresponding European Application No. 22177184.3, 8 pages.

* cited by examiner

*Primary Examiner* — Adam Z Minchella
*Assistant Examiner* — Davina E. Lee
(74) *Attorney, Agent, or Firm* — Nixon & Vanderhye PC

(57) ABSTRACT

A disposable patch electrode structure comprises a front flap and a main structure, which is attached to skin for a bio-signal measurement, the patch electrode structure feeding electrical bio-signals to a bio-signal device separate from the patch electrode structure. The front flap is separated from the main structure by a non-enclosing front flap cut, material of the front flap being thus formed as continuous material of the main structure. Materialistic connection of the continuous material between a rear section of the front flap at a non-enclosing side of the front flap cut and the main structure allows tilt of the front flap with respect to the main structure in response to rise of a frontal section of the front flap with respect to the main structure. The front flap is fully surrounded by the main structure. The front flap comprises contact electrodes at the frontal section, the contact electrodes being both connected with measurement electrodes of the main structure through conductors via the materialistic connection and connectable with counter-electrodes of a connector separate from the patch electrode structure.

12 Claims, 3 Drawing Sheets

(58) Field of Classification Search
CPC ...... A61B 2560/0443; A61B 2560/045; A61B 2560/0456; A61B 5/6833; A61B 2562/166; A61B 5/6802–6807
See application file for complete search history.

DISPOSABLE PATCH ELECTRODE STRUCTURE AND CONNECTOR OF BIO-SIGNAL MEASUREMENT SYSTEM, BIO-SIGNAL MEASUREMENT SYSTEM AND METHOD OF CONNECTING WITH DISPOSABLE PATCH ELECTRODE STRUCTURE

FIELD

The invention relates to a disposable patch electrode structure and a connector of bio-signal measurement system, a bio-signal measurement system and a method of connecting with a disposable patch electrode structure.

BACKGROUND

An electronic device, which measures bio-signals such as ECG (ElectroCardioGram) and EEG (ElectroEncephaloGram), must be well contacted with the electrodes that are in contact with the body and mechanically reliably fixed to its support.

Typically there is at least some electromechanical part for connecting and fixing the non-disposable bio-signal measurement device into the disposable single-use electrode part. An electromechanical connector is a both complicated and expensive part to manufacture and assemble on the disposable patch electrode. Because the patch electrode will be disposed after only a single use, also electromechanical connector is discarded with the patch electrode.

BRIEF DESCRIPTION

The present invention seeks to provide an improvement in the electromechanical connection.

The invention is defined by the independent claims. Embodiments are defined in the dependent claims.

If any of the embodiments does not fall under the scope of the independent claims, such an embodiment should to be interpreted as useful example for understanding features of the invention.

LIST OF DRAWINGS

Example embodiments of the present invention are described below, by way of example only, with reference to the accompanying drawings, in which FIG. 1 illustrates an example of a disposable patch electrode structure that comprises a front flap and a main structure and a connector viewed from an upper angle;

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may also contain features/structures that have not been specifically mentioned. All combinations of the embodiments are considered possible if their combination does not lead to structural or logical contradiction.

It should be noted that while Figures illustrate various embodiments, they are simplified diagrams that only show some structures and/or functional entities. The connections shown in the Figures may refer to physical connections. It is apparent to a person skilled in the art that the described apparatus may also comprise other functions and structures than those described in Figures and text. It should be appreciated that details of some functions, structures, and the signalling used for measurement and/or connection are irrelevant to the actual invention. Therefore, they need not be discussed in more detail here.

Figure 1:
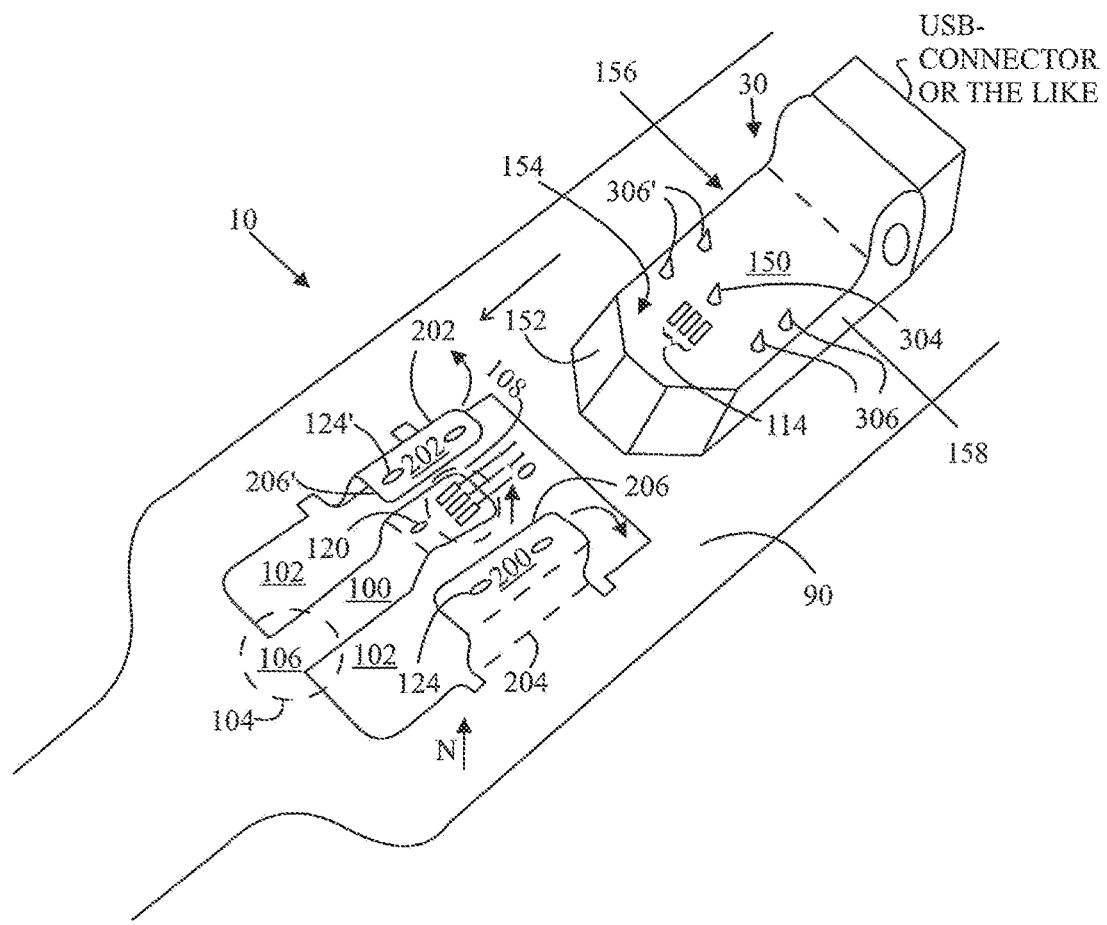

FIG. 1 illustrates a disposable patch electrode structure 10 that comprises a front flap 100 and a main structure 90. The patch electrode structure 10 is a piece of sheet that may be narrow like a band or broad like a wider planar surface and it is often fairly thin. The dimensions of the patch electrode structure 10 may resemble those of sheet of plastic, paper, board or cloth. The patch electrode structure 10 is configured to be attached to skin of a mammal such as a human being for a bio-signal measurement. The bio-signal may be related to body movement, body temperature, heart rate variability, electrocardiogram, electromyogram, electroencephalogram or the like for example. During a measurement, the patch electrode structure 10 feeds directly or indirectly electrical bio-signals to a non-disposable bio-signal device 20 that is separate from the patch electrode structure 10. The disposable patch electrode structure 10 may have a PET-layer.

The front flap 100 that is thin in a similar manner to the patch electrode structure 10 is separated from the main structure 90 by a non-enclosing front flap cut 102 that does not fully enclose or encircle an area of the patch electrode structure 10. The front flap 100 is attached and thus hinged at a rear side 104 with the main structure 90. Material of the front flap 100 thus forms a continuous materialistic connection 106 with the main structure 90 because their basic structure is the same or similar. The front flap 100 is thus integrated materialistically with the main structure 90.

The materialistic connection 106 of the continuous material between a rear section 104 of the front flap 100 at a non-enclosing side of the front flap cut 102 and the main structure 90 allows a tilt of the front flap 100 with respect to the main structure 90 in response to rise of a frontal section 108 of the front flap 100 with respect to the main structure 90. The frontal section 108 of the front flap 100 rises when tilted in a direction of a normal N of the main structure 90. The frontal section 108 is opposite to the rear section 104.

The front flap 100 is fully surrounded by the main structure 90 in a plane of the disposable patch electrode structure 10.

Figure 4:
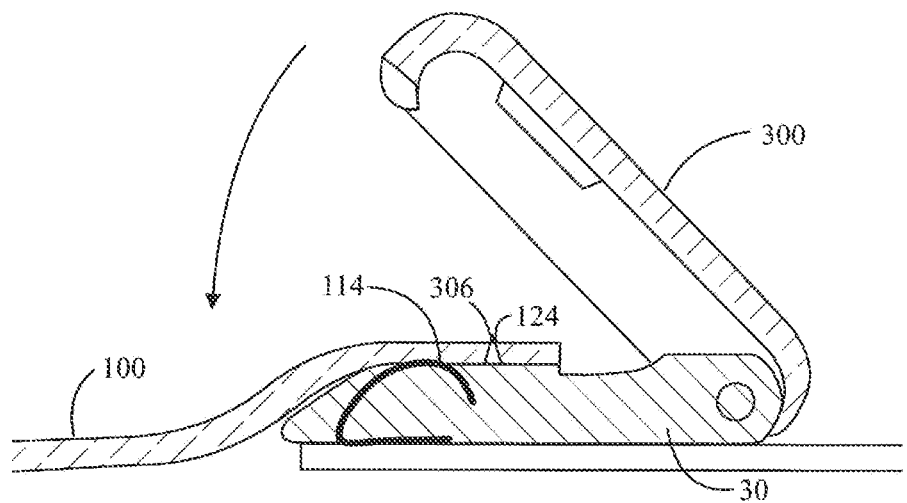
FIG. 4 illustrates an example of a cover of the connector.

The front flap 100 comprises contact electrodes 110 at the frontal section 108. The contact electrodes 110 may be AgCl-printed electrodes, for example (AgCl means silver chloride). The contact electrodes 110 are on one side of the front flap 100 and can be understood to be a "backside" of the front flap 100 although the contact electrodes 110 are drawn visible on the front flap 100 in FIGS. 1 and 4. The contact electrodes 110 are on the same side as measurement electrodes 112 that are configured to be touching the skin of a mammal during a bio-signal measurement. As can be seen in FIG. 4, the counter-electrodes 114 can contact with the contact electrodes 110 when the contact electrodes 110 are on the "backside" of the front flap 100 i.e. on the side that comes in contact with the counter-electrodes 114. The contact electrodes 110 are both connected with the measurement electrodes 112 of the main structure 90 through conductors 116 via the materialistic connection 106 and configured to connect with counter-electrodes 114 of a connector 30 separate from the patch electrode structure 10. The counter-electrodes 114 may be flexible, spring-like curves of metal, for example.

Figure 2A:
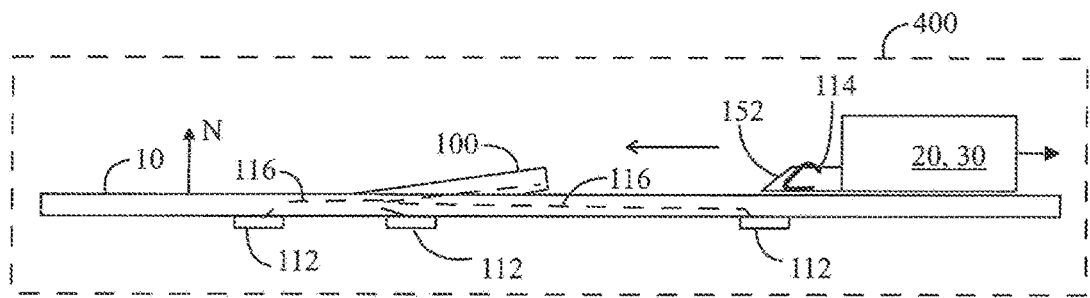
FIG. 2A to 2C illustrates an example of the disposable patch electrode structure a front flap of which is approached and connected with by a connector.
Figure 2B:
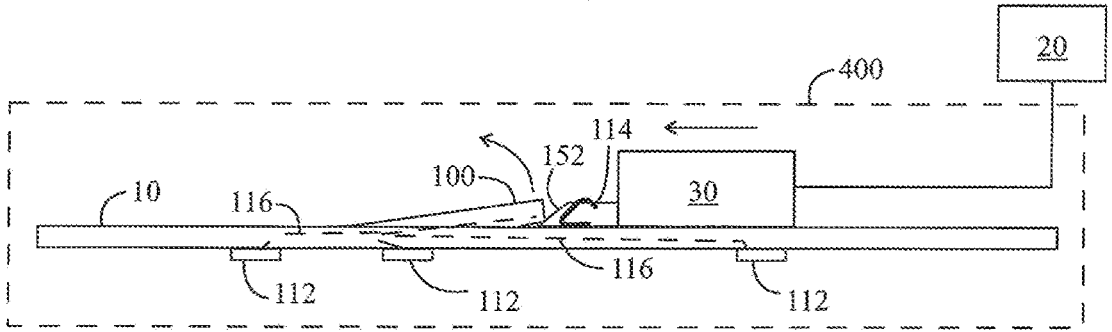
Figure 2C:
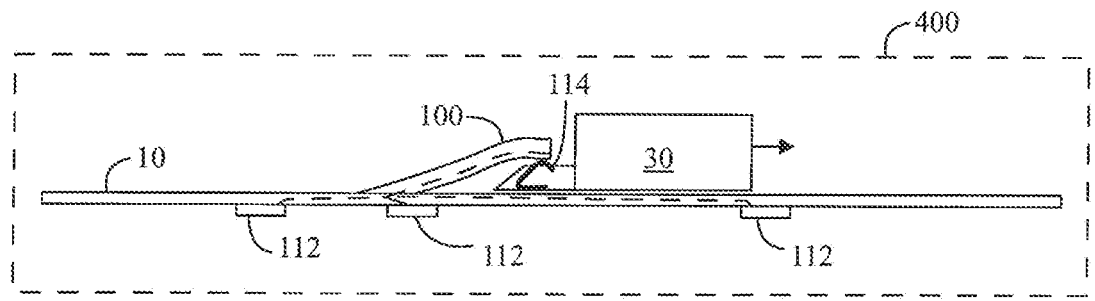

FIGS. 2A, 2B and 2C illustrate an example when the connector 30 is on the patch electrode structure 10. In FIG. 2A, the connector 30 is at a distance from the front flap 100. In FIG. 2B, the connector 30 is in contact with the front flap 100 and about to raise the front flap 100. In FIG. 2C, the connector 30 has raised the front flap 100 and the contact electrodes 110 are in contact with the counter electrodes 114. FIG. 1 also illustrates an example where the connector 30 includes the bio-signal measurement device 20. FIG. 2, in turn, illustrates an embodiment, where the bio-signal measurement device 20 is in wired connection with the connector 30.

In an embodiment, the front flap 100 comprises at least one mechanical coupling element 120 for a mechanical connection with the connector 30. The at least one mechanical coupling element 120 may comprise a hole or a weakened area i.e. a preform of a hole, for example.

In an embodiment, the disposable patch electrode structure 10 further may comprise a first side flap 200 and a second side flap 202.

In embodiment, the first side flap 200 may be separated from the patch electrode structure 10 by a non-enclosing first side flap cut 102' which may be connected or included in the non-enclosing front flap cut 102. The first side flap cut 102' may be united with the front flap cut 102 and they may form a single flap cut unseparable from each other. Material of the first side flap 200 is thus formed as continuous material of the main structure 90 such that materialistic connection 206 of the continuous material between a rear section 204 of the first side flap 200 at a non-enclosing side of the first side flap cut 200 and the main structure 90 are configured to allow tilt of the first side flap 200 in a direction of a normal N of the main structure 90 with respect to the main structure 90. The tilt may be caused by a face 152 of the connector 30.

The second side flap 202 may separated from the patch electrode structure 10 by a non-enclosing second side flap cut 102", which may be connected or included in the non-enclosing front flap cut 102. The second side flap cut 102" may be united with the front flap cut 102 and or the first side flap cut 102' and they may form a single flap cut unseparable from each other. Material of the second side flap 202 is thus formed as continuous material of the main structure 90 such that materialistic connection 206' of the continuous material between a rear section 204' of the second side flap 202 at a non-enclosing side of the second side flap cut 202 and the main structure 90 is configured to allow tilt of the second side flap 202 with respect to the main structure 90.

The first side flap 200 and the second side flap 202 may face each other spaced by a predetermined gap 208 therebetween when raised against the sides of the connector 30. The predetermined gap 208 may be matched with the connector 30. The first side flap 200 and the second side flap 202 are configured to tilt in opposite directions with respect to each other based on the continuous materialistic connections 206, 206'. In addition to that, the first side flap 200 and the second side flap 202 are configured to tilt in a direction perpendicular to the tilt of the front flap 100 while the front flap 100, the first side flap 200 and the second side flap 202 rise to same direction parallel to the normal N of the main structure 90. That is, the front flap 100, the first side flap 200 and the second side flap 202 rise above the main structure 90 on the same side of the patch electrode structure 10.

The frontal section 108 of the front flap 100 may be configured to face to or reside within the gap 208 between the first side flap 200 and the second side flap 202.

In an embodiment, the first side flap 200 may comprise at least one mechanical coupling element 124 and the second side flap 202 comprises at least one mechanical coupling element 124' for a mechanical contact with a connector 30. The mechanical coupling element 124, 124' may be holes or a weakened areas in the first side flap 200 and the second side flap, respectively.

Figure 5:
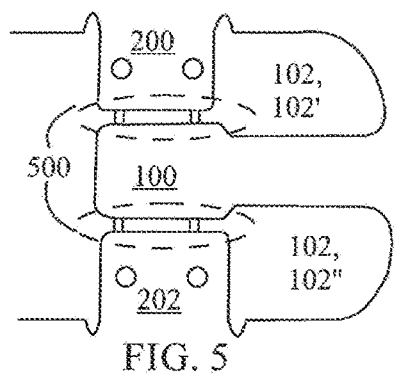
FIG. 5 illustrates an example of breakout tabs connecting the flaps.

In an embodiment an example of which is illustrated in FIG. 5, the front flap 100 and the first side flap 200 and the second side flap 202 may be materialistically connected with each other by at least one breakout tab 500 prior to a physical and/or electrical contact with the connector 30 and the at least one breakout tab 500 may break in response to connection between the patch electrode structure 10 and the connector 30. That is, the front flap 100 and the first side flap 200 and the second side flap 202 may be left with this kind of physical connection during manufacturing phase when making the front flap cut 102 and/or the first and second side flap cut 102, 102', 102". In more detail, the breakout tab 600 may break when the connector 30 is pushed forward for the connection with the contact electrodes 110.

FIG. 1 also shows the connector of the bio-signal measurement system. The connector 30 comprises a non-disposable base structure 150 with a face 152 and counter-electrodes 114 on an outer surface 154 next to the face 152.

The base structure 150 is configured to be slid on a main structure 90 of the disposable patch electrode structure 10 toward the front flap 100 of the patch electrode structure 10 with the face 152 ahead, the slide is shown with arrow (perpendicular to normal N) in FIG. 2A. The connector 30 is configured to be slid toward or up to the rear section 104 of the front flap 100.

As illustrated in FIG. 2B, the face 152 is configured to cause the frontal section 108 of the front flap 100 to rise and slide on the connector 30. That frontal section 108 can rise or diverge in a tilting manner in the direction of the normal N of the main structure 90 is based on materialistic connection 106 between the rear section 104 of the front flap 100 and the main structure 90 that is configured to allow tilt of the front flap 100 with respect to the main structure 90. As a result, the rear section 104 is like a hinge that bends in response to tilting rise of the frontal section 108 of the front flap 100 with respect to the main structure 90. The frontal section 108 is at an opposite end to the rear section 104.

The connector 30 is configured to cause the counter-electrodes 114 and the contact electrodes 110 to approach each other in response to the slide of the connector 30 toward the front flap 100 and when in contact with the front flap toward the rear section 104 of the front flap 100. When slid close to each other the contact electrodes 110 and the counter-electrodes 114 finally match together for an electrical contact.

Figure 3:
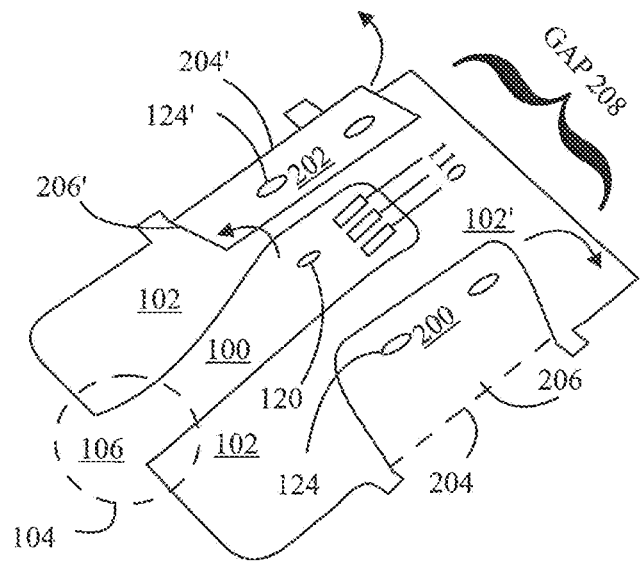
FIG. 3 illustrates an example of the front and side flaps when they are rising in a direction parallel to a normal of the main structure.

In an embodiment as illustrated in FIGS. 2B and 3, the face 152 is configured to enter a predetermined gap 208 matched for the connector 30 between a first side flap 200 and a second side flap 202 of the patch electrode structure 10. Then the connector 30, as it is moving on the surface of the patch electrode structure 10, may cause the first side flap 200 and the second side flap 202 to rise in a tilting manner, and cause them lean against sides 156, 158 of the connector 30.

In an embodiment an example of which is illustrated in FIG. 4, the connector 30 may comprise a lid or cover 300, which is configured to be applied on the front flap 100, and potentially also the first side flap 200 and the second side flap 202. Then the cover 300 may press the contact electrodes 110 and the counter-electrodes 114 against each other tightly for a reliable electric contact therebetween. The closed cover 300 may cause enough pressure for a proper electric coupling and potentially also mechanical attachment such that no other attachment is required. In this embodiment, the counter-electrode 114 may be a pad that is not elastic or springy (the counter-electrode 114 in FIG. is drawn springy). However, other mechanical and electrical coupling arrangement may also be used.

In an embodiment an example of which is illustrated in FIG. 1, the connector 30 may comprise at least one mechanical coupling element 304 for the front flap 100. Additionally in an embodiment, the connector 30 may comprise at least one mechanical coupling element 306 for the first side flap 200 and at least one mechanical coupling element 306' for the second side flap 202 on the outer surface 154 next to the face 152 for a mechanical connection between the disposable patch electrode structure 10 and the connector 30. The mechanical coupling elements 304, 306, 306' may be pins or the like. The pins may be made of metal or plastic, for example. The mechanical coupling element 304, 306, 306' may pass through the holes or weakened areas 120, 124, 124' of the disposable patch electrode structure 10 for a reliable mechanical connection between the disposable patch electrode structure 10 and the connector 30.

In an embodiment, the connector 30 may be a non-disposable bio-signal measurement device 20, be connected in a wired manner or a wireless manner with the bio-signal measurement device or be a part of the bio-signal measurement device with or without wires. The wired connection between the connector 30 and the bio-signal measurement device 20 may be through an USB-connector or the like (see FIGS. 1 and 2B). However, the connector 30 may an independent apparatus such as the bio-signal measurement device 20 that only connects with the disposable patch electrode structure 10. Hence, the connector 30 does not necessarily have the USB-connector.

Figure 6:
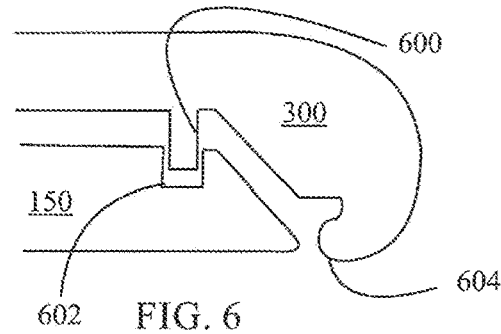
FIG. 6 illustrates an example of the cover with a cutting extension and a hook.

FIG. 6 illustrates an example of the cover 300 of the connector 30 that comprises at least one cutting extension 600 such as a spike or a blade, and the base structure 150 of the connector 30 comprises a hollow 602 for each of the at least one cutting extension 600. When the disposable patch electrode structure 10 is between the cover 300 and the base structure 30 and the cover 300 is closed, the at least one cutting extension 600 may cut a hole in the disposable patch electrode structure 10 and penetrate it. The cover 300 remains continuously shut after closing until it is time to dispose the disposable patch electrode structure 10. While the cover 300 is closed, the at least one cutting extension 600 keeps the disposable patch electrode structure 10 in place in addition the friction caused by pressure because the at least one cutting extension extends through the disposable patch electrode structure 10 and is firmly fixed to the cover 300 at one end and is firmly within the hollow 602 at the other end.

In an embodiment shown in FIG. 6, the cover 300 may comprise a hook structure 604 that is configured to go below the base structure 150 such that the cover is locked with the edge of the base structure 150. In this manner, the cover 300 is locked in an immobile position and causes constant pressure to keep the contact electrodes 110 and the counter electrodes 114 well in place and touch with each other.

Figure 7:
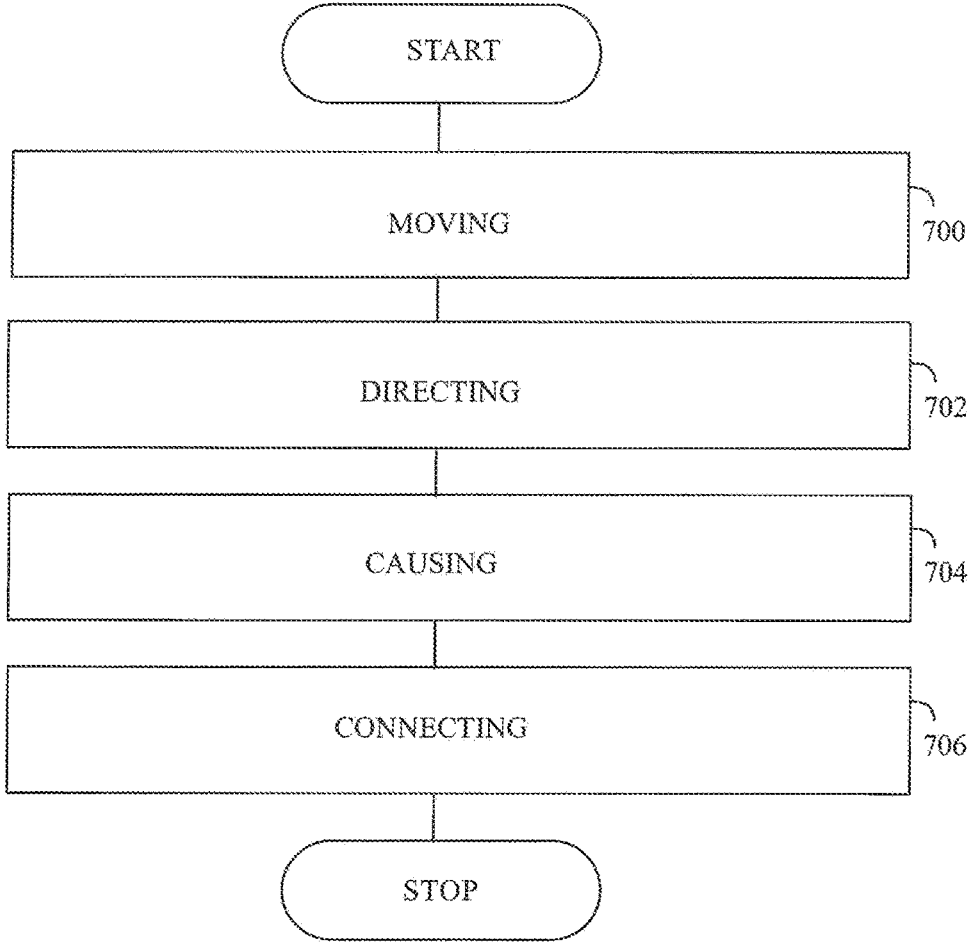
FIG. 7 illustrates of an example of a flow chart of a connecting method.

FIG. 7 is a flow chart of the measurement method. In step 700, a connector 30 and the disposable patch electrode structure 10 are moved in a sliding manner with respect to each other while the connector 30 is on a surface of the disposable patch electrode structure 10.

In step 702, the movement of the connector 30 is directed with the face 152 ahead toward a front flap 100 of the patch electrode structure 10, the front flap 100 being separated from a main structure 90 by a non-enclosing front flap cut 102, material of the front flap 100 being thus formed as continuous material of the main structure 90 and the front flap 100 being fully surrounded by the main structure 90, and contact electrodes 110 of the front flap 100 being connected both with measurement electrodes 112 of the patch electrode structure 10 through conductors 116 and connectable with the counter-electrodes 114 separate from the patch electrode structure 10, convey electrical bio-signals to a non-disposable bio-signal device 20.

In step 704, the front flap 100 is caused to rise in a tilting manner with respect to the main structure 90 in response to contact with the face 152 of the connector 30 while the connector 30 is moving and pushing the frontal flap 100, the tilt being based on materialistic connection 106 of continuous material between the rear section 104 of the front flap 100 and the main structure 90 that allows the tilt of the front flap 100 with respect to the main structure 90.

In step 706, the contact electrodes 110 and the counter-electrodes 114 are connected together for an electrical contact after their approach of each other based on the sliding movement on the patch electrode structure 10.

It will be obvious to a person skilled in the art that, as technology advances, the inventive concept can be implemented in various ways. The invention and its embodiments are not limited to the example embodiments described above but may vary within the scope of the claims.

What is claimed is:

1. A disposable patch electrode structure, the patch electrode structure comprising:
  a front flap and a main structure, which is configured to be attached to skin for a bio-signal measurement, the patch electrode structure being configured to feed electrical bio-signals to a bio-signal device separate from the patch electrode structure; wherein:
  the front flap is separated from the main structure by a non-enclosing front flap cut, material of the front flap being thus formed as continuous material of the main structure;
  a material connection of the continuous material between a rear section of the front flap at a non-enclosing side of the front flap cut and the main structure is configured to allow tilt of the front flap with respect to the main structure in response to a rise of a frontal section of the front flap with respect to the main structure, the frontal section being opposite to the rear section;
  the front flap is fully surrounded by the main structure;
  the front flap comprises contact electrodes at the frontal section, the contact electrodes being both connected with measurement electrodes of the main structure through conductors via the material connection and configured to connect with counter-electrodes of a connector separate from the patch electrode structure; and the connector comprises a non-disposable base structure with a face, the face being configured to enter a predetermined gap matched for the connector between a first side flap and a second side flap of the patch electrode structure, and cause the first side flap and the second side flap to rise in a tilting manner, and lean against sides of the connector.

2. The disposable patch electrode structure of claim 1, wherein the front flap comprises at least one mechanical coupling element for a mechanical connection with the connector.

3. The disposable patch electrode structure of claim 1, wherein:

the first side flap is separated from the patch electrode structure by a non-enclosing first side flap cut, material of the first side flap being thus formed as continuous material of the main structure such that a material connection of the continuous material between a rear section of the first side flap at a non-enclosing side of the first side flap cut and the main structure is configured to allow tilt of the first side flap with respect to the main structure;

the second side flap is separated from the patch electrode structure by a non-enclosing second side flap cut, material of the second side flap being thus formed as continuous material of the main structure such that a material connection of the continuous material between a rear section of the second side flap at a non-enclosing side of the second side flap cut and the main structure being configured to allow tilt of the second side flap with respect to the main structure;

a first end section of the first side flap and a second end section of the second side flap are configured to face each other spaced by the predetermined gap therebetween matched with the connector, and the first side flap and the second side flap are configured to tilt in opposite directions with respect to each other based on the continuous material connections, and in a direction perpendicular to the tilt of the front flap while the front flap, the first side flap and the second side flap are configured to rise in a direction parallel to the normal of the main structure; and the frontal section of the front flap is configured to face or reside within the gap between the first side flap and the second side flap.

4. The disposable patch electrode structure of claim 3, wherein the first side flap comprises at least one mechanical coupling element and the second side flap comprises at least one mechanical coupling element for a mechanical contact with a connector.

5. The disposable patch electrode structure of claim 3, wherein the front flap and the first side flap and the second side flap are materially connected with each other by at least one breakout tab prior to a contact with the connector, and the at least one breakout tab is configured to break in response to connection between the patch electrode structure and the connector.

6. A connector of a bio-signal measurement system, the connector comprising:

a non-disposable base structure with a face and counter-electrodes on an outer surface next to the face, the base structure being configured to be slid on a main structure of a disposable patch electrode structure toward a front flap of the patch electrode structure with the face ahead, a frontal section of the front flap comprising contact electrodes, which are connected with measurement electrodes of the patch electrode structure through conductors; wherein:

the face is configured to cause the frontal section of the front flap to rise and slide thereon based on a material connection between a rear section of the front flap and the main structure that is configured to allow tilt of the front flap with respect to the main structure in response to a tilting rise of a frontal section of the front flap with respect to the main structure, the frontal section being opposite to the rear section;

the connector is configured to cause the counter-electrodes and the contact electrodes to approach each other in response to the slide of the connector toward a rear section of the front flap, where the contact electrodes and the counter-electrodes match together for an electrical contact; and the face is configured to enter a predetermined gap matched for the connector between a first side flap and a second side flap of the patch electrode structure, and cause the first side flap and the second side flap to rise in a tilting manner, and lean against sides of the connector.

7. The connector of claim 6, wherein the connector comprises a cover, which is configured to be applied on the front flap, the first side flap and the second side flap, the cover pressing the contact electrodes and the counter-electrodes against each other.

8. The connector of claim 6, wherein the connector comprises at least one mechanical coupling element for the front flap, at least one mechanical coupling element for the first side flap and at least one mechanical coupling element for the second side flap on the outer surface next to the face for a mechanical connection between the disposable patch electrode structure and the electrical device.

9. The connector of claim 6, wherein the connector is a part of a non-disposable bio-signal measurement device.

10. A bio-signal measurement system, the bio-signal measurement system comprising:

a disposable patch electrode structure comprising:

a front flap and a main structure, which is configured to be attached to skin for a bio-signal measurement, the patch electrode structure being configured to feed electrical bio-signals to a non-disposable bio-signal device; wherein:

the front flap is separated from the main structure by a non-enclosing front flap cut, material of the front flap being thus formed as continuous material of the main structure;

a material connection of the continuous material between a rear section of the front flap at a non-enclosing side of the front flap cut and the main structure is configured to allow tilt of the front flap with respect to the main structure in response to rise of a frontal section of the front flap, the frontal section being opposite to the rear section;

the front flap is fully surrounded by the main structure; and the front flap comprises contact electrodes at the frontal section, the contact electrodes being both connected with measurement electrodes of the main structure through conductors via the material connection and configured to connect with counter-electrodes of a connector separate from the patch electrode structure; and a connector comprising:
- a non-disposable base structure with a face and counter-electrodes on an outer surface next to the face, the base structure being configured to be slit on a main structure of a disposable patch electrode structure toward a front flap of the patch electrode structure with the face ahead, a frontal section of the front flap comprising contact electrodes, which are both connected with measurement electrodes of the patch electrode structure through conductors and configured to connect with the counter-electrodes separate from the patch electrode structure; wherein:
- the face is configured to cause the frontal section of the front flap to rise in a tilting manner based on a material connection of continuous material between a rear section of the front flap and the main structure that is configured to allow the tilt of the front flap with respect to the main structure, the frontal section being opposite to the rear section;
- the electrical device is configured to cause the counter-electrodes and the contact electrodes to approach each other in response to the slide of the electrical device toward a rear section of the front flap, where the contact electrodes and the counter-electrodes match together for an electrical contact; and
- the face is further configured to enter a predetermined gap matched for the connector between a first side flap and a second side flap of the patch electrode structure, and cause the first side flap and the second side flap to rise in a tilting manner, and lean against sides of the connector.

11. The bio-signal measurement system of claim 10, wherein the connector comprises at least one cutting extension, and the base structure of the connector comprises a hollow for each of the at least one cutting extension; and the at least one cutting extension is configured to cut a hole in the disposable patch electrode structure that is between a cover and the base structure and penetrate the disposable patch electrode structure in response to closure of the cover.

12. A method of connecting a connector with a disposable patch electrode structure of a bio-signal measurement system, the method comprising:
- moving in a sliding manner a connector and the disposable patch electrode structure with respect to each other while the connector is on a surface of the disposable patch electrode structure;
- directing the movement of the connector with a face ahead toward a front flap of the patch electrode structure, the front flap of which is separate from a main structure by a non-enclosing front flap cut, material of the front flap being thus formed as continuous material of the main structure and the front flap being fully surrounded by the main structure, contact electrodes, which are both connected with measurement electrodes of the patch electrode structure through conductors and connectable with counter-electrodes separate from the patch electrode structure, convey-electrical bio-signals to a non-disposable bio-signal device, wherein the front flap comprises the contact electrodes, which are configured to convey electrical bio-signals to a non-disposable bio-signal device;
- causing a tilting rise of the front flap with respect to the main structure in response to contact with the face of the connector while the connector is moving and pushing the frontal flap, the tilt being based on a material connection of continuous material between a rear section of the front flap and the main structure that allows the tilt of the front flap with respect to the main structure; and
- connecting the contact electrodes and the counter-electrodes together for an electrical contact after their approach of each other based on the sliding movement on the patch electrode structure;
- wherein the face is configured to enter a predetermined gap matched for the connector between a first side flap and a second side flap of the patch electrode structure, and cause the first side flap and the second side flap to rise in a tilting manner, and lean against sides of the connector.

* * * * *